US005423744A

United States Patent [19]

Gencheff et al.

[11] Patent Number: 5,423,744

[45] Date of Patent: Jun. 13, 1995

[54] CATHETER SYSTEM FOR THE DEPLOYMENT OF BIOLOGICAL MATERIAL

[76] Inventors: Nelson Gencheff, 597 Lakewood Ave., Marquette, Mich. 49855; Carl W. Christensen, 7463 N. Beach Ct., Fox Point, Wis. 53217

[21] Appl. No.: 142,617

[22] Filed: Oct. 25, 1993

Related U.S. Application Data

[63] Continuation-in-part of Ser. No. 995,105, Dec. 22, 1992, Pat. No. 5,256,141.

[51] Int. Cl.[6] .................... A61M 31/00

[52] U.S. Cl. .................... 604/53; 604/21; 604/101; 604/107

[58] Field of Search .................... 604/20, 21, 52, 53, 604/96, 101, 104–107, 113, 114; 607/115, 116, 120, 122, 124, 126, 127

[56] References Cited

U.S. PATENT DOCUMENTS

| | | | |
|---|---|---|---|
| 4,423,725 | 1/1984 | Baran et al. . | |
| 4,610,662 | 9/1986 | Weikl et al. . | |
| 4,636,195 | 1/1987 | Wolinsky . | |
| 4,708,718 | 11/1987 | Daniels . | |
| 4,776,349 | 10/1988 | Nashef et al. | 128/786 |
| 4,785,823 | 11/1988 | Eggers et al. . | |
| 4,944,745 | 7/1990 | Sogard et al. . | |
| 5,047,028 | 9/1991 | Qian . | |
| 5,129,883 | 7/1992 | Black . | |
| 5,135,484 | 8/1992 | Wright | 604/82 |
| 5,279,299 | 1/1994 | Imran | 128/642 |
| 5,279,546 | 1/1994 | Misone et al. | 604/22 |
| 5,286,254 | 2/1994 | Shapland et al. | 604/21 |
| 5,304,120 | 4/1994 | Crandell et al. | 604/52 |

FOREIGN PATENT DOCUMENTS

| | | |
|---|---|---|
| 2513868 | 10/1975 | Germany . |
| 3806458 | 9/1989 | Germany . |
| 2219510 | 12/1989 | United Kingdom . |
| 721110 | 3/1980 | U.S.S.R. . |
| 1069826 | 1/1984 | U.S.S.R. . |
| 1228821 | 5/1986 | U.S.S.R. . |
| 85/02779 | 7/1985 | WIPO . |
| 91/16945 | 11/1991 | WIPO . |

OTHER PUBLICATIONS

Haudenschild, C. C., "Growth control of endothelial cells in atherogenesis and tumor angiogenesis", Advances in Microcirculation, 9 (1980) 226–251.

Ross, R., "The pathogenesis of athersclerosis", in Braunwald, E. (ed): Heart Disease, 3d Edition, Saunders WB, 1988, 1135–1152.

Ross, R. and J. Glomset, "Athersclerosis and arterial smooth muscle cell", Science, 180 (1973) 1332.

Schneider et al., "Confluent durable endothelialization of endarterectonized baboon aorta by early attachment of cultured endothelial cells", *J Vasc Surg*, 11:365–372, 1990.

Flugelman et al., "Genetically engineered endothelial cells rema adherent and viable after stent deployment and exposure to flow *in viro*", *Circ Res* 70: 348–354, 1992.

Jarrell et al., "Use of freshly isolated capillary endothalial cells for the immediate establishment of a monolayer on a vascular graft at surgery", *Surgery* 100(2):392–399, 1986.

*Primary Examiner*—Corrine Maglione

*Attorney, Agent, or Firm*—Haugen and Nikolai

[57] ABSTRACT

The invention involves a system for the deployment of biologically/pharmacologically active materials in a bodily passage, particularly in vascular wall tissue, in the form of a multi-lumen catheter having several serially situated zones. One embodiment has a dispersion zone adapted to address a vascular segment and having a dispersion chamber with a pattern of openings for deploying biologically active materials supplied through an externally connected lumen. An expandable array of conductor elements is provided in the dispersion zone to apply a controlled electrical field to the biologically active material at the surface of deployment. Spaced inflatable balloons define proximal and distal occlusion zones for temporarily occluding normal vascular blood flow in conjunction with a flow bypass lumen that connects proximal and distal infusion port zones flanking the occlusion zones and maintaining blood flow about and beyond the vascular segment. A control system is provided for controlling operation of the deployment system including flexure of the conductor elements and the electrical input capable of the time-variable modulation of the charge applied by the electrode means.

24 Claims, 2 Drawing Sheets

CATHETER SYSTEM FOR THE DEPLOYMENT OF BIOLOGICAL MATERIAL

CROSS-REFERENCE TO RELATED APPLICATION

This application is a continuation-in-part of Ser. No. 07/995,105, filed Dec. 22, 1992, now U.S. Pat. No. 5,256,141.

BACKGROUND OF THE INVENTION

I. Field of the Invention

The invention is directed generally to a catheter or other invasive vascular navigating device intended to enable deployment of biologically active materials. More particularly, the invention involves a vascular catheter system for the electrical charge mediated deployment of biologically active materials into specific segments of living blood vessels. This includes transplanting biologically functional autologous vascular endothelium into blood vessels whose endothelium and subendothelial structures have been damaged as well as altering endothelial and subendothelial biology by the electrical application of metabolic activators or inhibitors.

II. Description of the Related Art

Coronary artery disease is a significant problem throughout the world, and it is among the major consequences of injured endothelial cells. If left to its natural history, coronary artery disease invariably leads to death. The past two decades of cardiovascular research have resulted in the birth and growth of interventional cardiovascular procedures which have made a major impact on the morbidity and mortality of patients with this disease. According to 1992 statistics, an estimated 750,000 patients with coronary artery disease will undergo coronary artery balloon angioplasty or atherectomy to open a blocked artery. However, since the first percutaneous transluminal coronary angioplasty (PTCA) performed in 1977 by Andreas Gruentzig, cardiovascular interventionalists have been witness to generally disappointing long-term results with respect to the post-PTCA vessel patency. Approximately 30% to 50% of the treated patients will have recurrence (restenosis) of their arterial obstructions and will require further angioplasty treatment or open heart surgery.

Restenosis of angioplasted vascular segments has prompted a multifaceted, international research campaign attempt to improve post-PTCA long-term vessel patency. Much of this research has been focused on improving balloon catheter designs, understanding lesion characteristics, improving patient selection for angioplasty procedures and elucidating the pathophysiology of restenosis.

A major cause of this restenosis is the absence or disruption of the normal cells (endothelial cells) that line the internal surface of a normal arterial segment. This cell lining, known as vascular endothelium, is often disrupted or destroyed by the atherosclerotic disease process and by the previously mentioned stenosis reduction or removal procedures. Maintaining vascular endothelial integrity is important as it performs a variety of vital functions necessary to support life. These functions are contingent upon the presence of morphologically intact and biologically functional endothelial cells and their intimate association with subendothelial structures. Disruption of the framework of this biological system causes the endothelial cells to become dysfunctional, and it is this critical event which sets the stage for the onset or recurrence of vascular disease and its devastating progression.

In this regard, vascular smooth muscle cell proliferation appears to be a pivotal event in the pathology of restenosis. Smooth muscle cell proliferation is, in part, triggered by the mitogenic properties of platelet-derived growth factor (PDGF). However, it is generally believed that more than one mitogenic activator is responsible for this process. There is further evidence suggesting that endothelial cells help to modulate vascular smooth muscle cell biology and that when endothelial cells become dysfunctional, vascular smooth muscle cells favor a synthetic (proliferative) state. Further discussion is provided by, for example, Haudenschild, C. C., "Growth control of endothelial cells in atherogenesis and tumor angiogenesis", Advances in Microcirculation, 9 (1980) 226–251; Ross, R., "The pathogenesis of atherosclerosis", in Braunwald, E. (ed): Heart Disease, 3d Edition, Saunders WB, 1988, 1135–1152; Ross, R. and J. Glomset, "Atherosclerosis and arterial smooth muscle cell", Science 180 (1973) 1332.

Since PTCA traumatizes vascular endothelium and subendothelial structures, it triggers a cascade of biological events which may lead to smooth muscle cell proliferation. To a great extent, this PDGF-mediated process may be held in check by platelet inhibitors and heparin sulfate. However, because PDGF, and other smooth muscle mitogens, are not only released by platelets, but also by dysfunctional endothelial cells, uncontrolled smooth muscle cell proliferation can still occur.

Vascular endothelial cells grow in an obligate monolayer attached by tight junctions and gap junctions. Maintenance of this structural design is essential for the normal biological function of endothelial cells and this framework is, in part, accomplished through a type IV collagen matrix upon which endothelial cells reside. If endothelial cells are unable to adhere to a given surface, they become nonviable. In vivo placement of endothelial cells upon this collagen matrix is inherently problematic because laminar flow produces forces of shear stress resulting in an intravascular environment which is not conducive for endothelial cell attachment. However, freshly endarterectomized aortas incubated in vitro, in a low flow, low pressure environment with homologous aortic endothelial cells for 20 minutes result in rapid endothelial cell attachment, as reported by Schneider et al, "Confluent durable endothelialization of endarterectomized baboon aorta by early attachment of cultured endothelial cells, *J Vasc Surg* 11:365–372, 1990. In vivo exposure of these attached cells to laminar blood flow and pressure for one hour yields a thromboresistant, confluent and durable monolayer. It has also been shown that in vitro seeding of genetically engineered endothelial cells onto catheter mounted stainless steel vascular stents remain not only adherent but also viable after stent expansion and exposure to in vitro pulsatile flow (Flugelman et al, "Genetically engineered endothelial cells remain adherent and viable after stent deployment and exposure to flow in vitro", *Circ Res* 70:348–354, 1992) Finally, endothelial cells freshly obtained from human fat and acutely seeded in vitro onto plasma coated dacron grafts for one hour, remain adherent and form confluent monolayers when exposed to flow for two hours at a shear stress of 0 to 80 dynes/$cm^2$ (Jarrell et al, "Use of freshly isolated capillary endothelial cells for the immediate establishment of a monolayer on a vascular graft at surgery, *Surgery* 100(2):392–399, 1986).

Since endothelial cells contain much of the biological armamentarium necessary to orchestrate the molecular events required to maintain a thromboresistant and homeostatic vascular milieu, it follows that if a device were available to quickly reestablish a normal endothelial monolayer immediately following angioplasty or atherectomy, the incidence of restenosis could be significantly reduced and possibly eliminated. The high flow velocities of the intravascular hemodynamic environment, however, technically limits in vivo application of endothelial seeding onto denuded intravascular surfaces.

Invasive implant devices including catheters have been proposed which deliver an electric charge to remote areas of a patient's body. One such catheter device intended for relatively long-term use has been devised that applies a unidirectional negative charge to discourage microbial growth at the implant interface surface. This is shown in UK patent application GB 2 219 510. A PCT application WO 85/02779 discloses a catheter for treating tumors which delivers a high frequency heat producing current to the tumor tissue.

Other catheter devices are known that employ a plurality of spaced fluid inflated balloon devices for isolating and treating segments of blood vessels and other body passages such as trachea and urethra. Examples of such devices which also allow bypass flow around an isolated segment are found in Weikl et al (U.S. Pat. No. 4,610,662) and Baran et al (U.S. Pat. No. 4,423,725). A further multiple balloon device is illustrated in Wolinsky (U.S. Pat. No. 4,636,195).

The present invention addresses this problem by providing a new device which includes a system for deployment of biologically active materials (endothelial cells) into specific segments of living blood vessels to be reseeded with new, autologously derived endothelial cells. The invention also provides for iontophoretic delivery of biologic/pharmacologic agents into these specific vascular segments. One design aspect of the device provides for significantly diminished blood flow in the specific vascular segments of interest for a time long enough, for example, to allow cultured endothelial cells to adhere to the vascular surface. This is accomplished by providing an integral bypass system to simultaneously re-establish blood flow beyond the isolated area.

OBJECTS OF THE INVENTION

Accordingly, it is a primary object of the present invention to provide a new catheter system which will enable the electrical charge mediated deployment of biologically active materials into specific segments of living blood vessels.

A further object of the invention is to provide a catheter system capable of the electrical application of metabolic activators and/or inhibitors for altering subendothelial biology.

Another object of the invention is to provide a catheter system for transplanting biologically functional autologous endothelial cells onto blood vessels whose endothelium and subendothelial structures have been mechanically or physically perturbed.

A still further object of the invention is to provide a catheter system capable of mechanically isolating a vascular segment of interest, and deploying biologically active materials and maintaining blood flow distal to the vascular segment of interest.

Yet another object of the invention is to provide a method of deploying biologically active materials including iontophoretic delivery of biologic/pharmacologic agents into vascular segments through an externally accessed dispersion chamber.

A yet still further object of the invention is to provide an expandable means for providing an electric field of desired strength proximate the endothelial or subendothelial surface to enhance the electrical charge mediated deployment of biologically active materials.

SUMMARY OF THE INVENTION

The present invention solves many of the problems associated with the deployment of biologically active materials in vascular segments in which the deployment requires a period of flow interruption, i.e., a time to establish the biologically active material in situ for the deployment to succeed. The biological deployment system of the invention may take many forms. One important form is concerned with charge mediated deployment of endothelial cells into vascular segments having damaged vascular endothelium. The invention also provides a method of preventing or reducing repeated vascular blockages in segments where stenoses have previously been invasively treated.

One successful embodiment is in the form of an endothelial deployment catheter device. The catheter is a multi-zone, multi-lumen device that interfaces a plurality of input/output peripherals proximally and provides working zones distally. In the working portion of the catheter, a pair of spaced fluid inflatable balloons having centers marked by radiopaque bands flank a controlled charge-mediated dispersion zone which includes an electrode to which a charge can be applied and a dispersion chamber or infusion lumen in contact with the electrode and having a plurality of openings through which with material of interest including an endothelial cell culture can be discharged into the vascular segment between the spaced balloons.

A further pair of zones flanking the pair of flow control balloons contain radially disposed openings which lead to a common guidewire/perfusion lumen which provides a continuous bypass conduit for blood to bypass the segment defined by the flow control balloons when one or both are inflated to reduce or curtail flow in the vascular segment of interest. A long vascular navigating zone is provided between the peripheral interface zone and the proximal isolation balloon to connect the system outside the patient. The distal portion of this zone includes the proximal bypass perfusion inflow ports.

The catheter is preferably constructed as an over-the-wire system and may conveniently be produced of quadraxially extruded polyethylene tube or similar material providing four internal lumens to accomplish the catheter functions. The lumens connect the various working zones with the peripheral interface zone. Thus, lumens independently connect the proximal and distal isolation or flow control balloons with pressure regulated fluid sources. A lumen is provided to connect the dispersion chamber with a source of the biologically active material to be delivered to the vascular segment and the guidewire/perfusion lumen carries the guidewire and includes the inlet and outlet ports for the bypass flow.

Deployment of the biologically active material through the externally accessed dispersion chamber is accomplished in conjunction with the operation of a pulsed or constant electric field provided by the externally connected electrode which is typically a perforated foil or mesh of a noble metal, such as platinum, overlaying the dispersion chamber and externally connected by a platinum wire. If operated in a pulsed mode, the pulse may be delivered by an electrical stimulator triggered by the patient's own ECG complex. The dispersion chamber of one model was 22 mm long and delivered materials through a pattern of perforations through an arc-shaped chamber that included about 240 degrees of the circumference of the catheter. The openings in the dispersion chamber cooperate with those in the electrode to produce a uniform delivery of the material contained in the dispersion chamber.

The surface electrode of the charge mediated dispersion zone may, if desired, be replaced or augmented with an array of radially spaced, axially disposed outwardly flexible conductors to deliver an electric charge and produce an electric field with enhanced radial uniformity or controlled radial asymmetry proximate to the endothelial or subendothelial surface of interest. Externally operable means are provided to expand or flex out the array of radially disposed conductors upon deployment and retract or collapse the conductors along the dispersion chamber during vascular navigation. The degree or relative amount of deployment of the radially disposed conductors is controlled by the operator using a calibrated deployment handle. Once deployed to the desired amount, the handle is then designed with the capability to be locked at a known position to maintain the conductor deployment at the set amount.

The preferred method for placement of the catheter at the vascular site includes inserting the catheter preloaded with the guidewire through a guide catheter advancing the guidewire through the vascular system beyond the vascular segment of interest to be treated. The deployment catheter device of the invention is delivered over the guidewire via the guidewire lumen. Using the radiopaque markers associated with the deployment catheter tip and isolation balloons, the dispersion chamber is positioned in the location to be treated, and the balloons are then inflated. Once positioned in place, the guidewire is withdrawn proximate to the infusion ports and a bypass flow establishes itself around the isolated segment. The electrode or other distributive charge providing means deployed is energized and the biologically active material, normally a culture of endothelial cells and/or metabolic activators or metabolic inhibitors to alter the endothelial and subendothelial biology are delivered through the dispersion chamber under the influence of the electric field controlled by the operator. After the cells have had time to attach or after delivery of the appropriate biologic/pharmacologic agent, as the case may be, the steps may be reversed and the system removed from the patient.

Balloon pressure is monitored using manometers or other well-known devices to prevent overpressurization as the purpose of the balloons is only to occlude flow, not expand vascular size. In addition, the dispersion chamber is typically provided with a one-way pressure relief valve which remains closed unless the relative pressure within the occluded vascular segment exceeds a predetermined pressure such as 100 mm Hg. The relief valve is typically 400 μm in diameter.

The deployment device of the invention facilitates and expedites reseeding of new, biologically functional, autologous endothelium and modulates subendothelial biology by the electrical application of growth activators and/or inhibitors in specific vascular segments previously perturbed. In addition, the device of the invention is decidedly useful for many iontophoretic delivery applications. The system can be used to apply a pulsed or constant direct current stimulus to transport pharmacologic agents including cardioactive drugs such as vasodilators and other materials, for example, to specific subendothelial vascular tissue sites of interest in conjunction with the placement of the deployment device. Thus, any drug or other material susceptible to iontophoretic transport implantation may also be delivered by the system. In this manner, positively or negatively charged ions of interest are driven into the tissue of interest utilizing an applied current differential in a well-known manner. The device of the invention, in this manner, provides what amounts to be a portable system which can be used to apply iontophoretic transport techniques to any selected vascular segment of interest.

BRIEF DESCRIPTION OF THE DRAWINGS

In the drawings, wherein like numerals designate like parts throughout the several views.

DETAILED DESCRIPTION

Figures 1, 2, 3, 4, 5, 6:
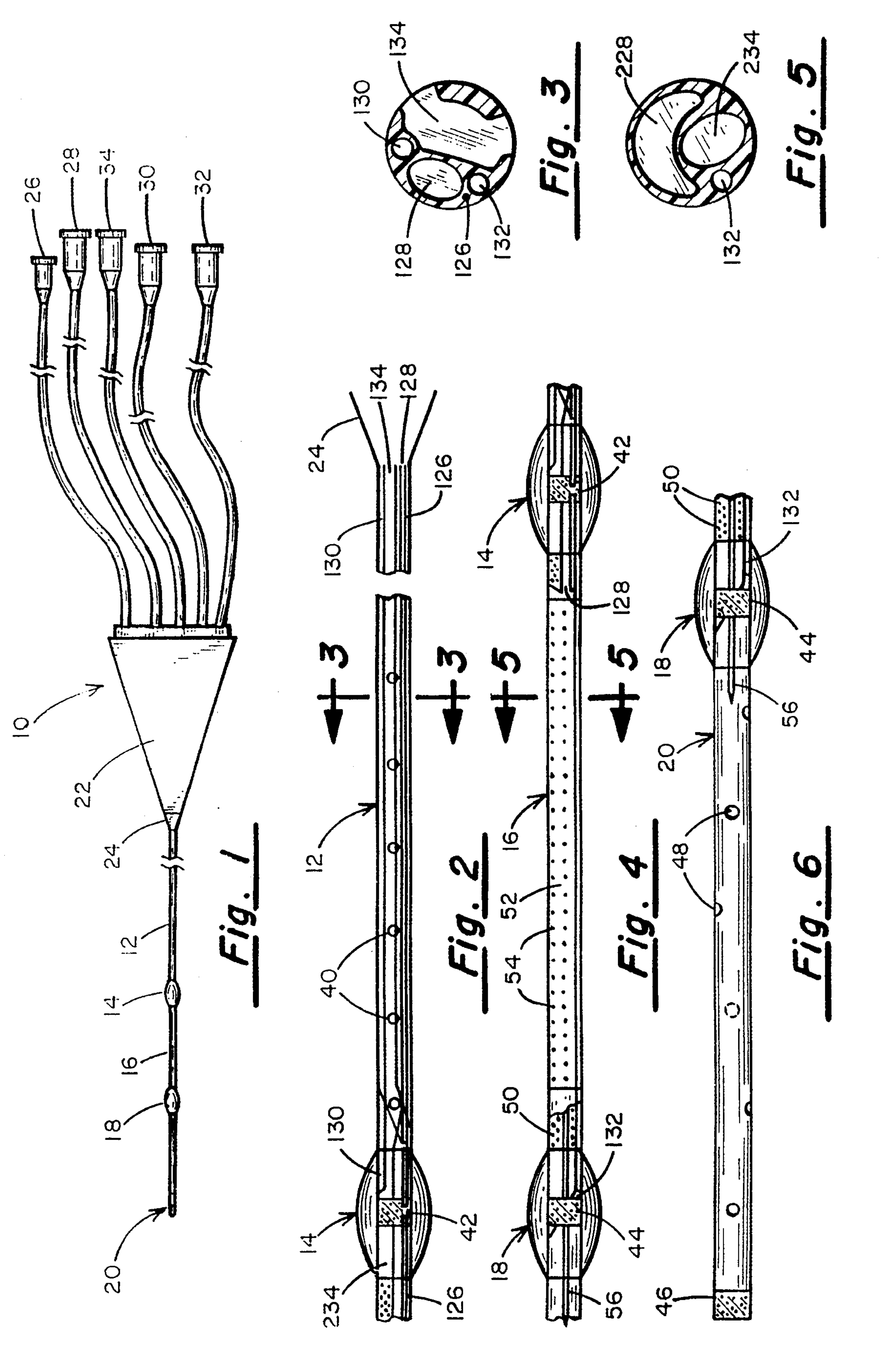
FIG. 1 is an overall schematic view of the endothelial deployment catheter device of the invention broken away where inordinate lengths are involved.
FIG. 2 is an enlarged fragmentary side view of a proximal zone of the catheter portion of the device of FIG. 1.
FIG. 3 is a sectional view taken along 3—3 of FIG. 2.
FIG. 4 is an enlarged fragmentary side view similar to that of FIG. 2 of the central zones of the catheter portion of the device of FIG. 1.
FIG. 5 is a sectional view taken along 5—5 of FIG. 4.
FIG. 6 is a view similar to those of FIGS. 2 and 4 depicting the distal zone of the catheter portion of the device.

FIG. 1 depicts an overall schematic view of the endothelial deployment device of the invention denoted generally at 10. The device includes an elongated catheter which itself is divided into a plurality of body invasive zones 12, 14, 16, 18 and 20 intended to navigate vascular passages and which connect to what may be described as a peripherals interface zone 22 located proximal of the body invasive zones and the body/catheter entry hub 24. The peripherals interface zone connects a plurality of externally accessible devices with the corresponding catheter lumens. These may include an electrical input/output single or multiple conductor plug or jack device 26, a drug or implant cell infusion port access 28, a proximal balloon inflation fluid passage port 30, a distal balloon infusion fluid port 32 and a guidewire/perfusion access port shown at 34. These are connected by appropriate means to the corresponding lumens of the catheter through the interface zone.

These and other types of access ports are common to such devices and the precise construction may vary according to the practices of those skilled in the art. For example, the guidewire or catheter is preferably constructed to be deployed using established over-the-wire vascular navigation techniques. Thus, the proximal guidewire port shown at 34 may be located, for example, close to the distal end of the proximal invasive catheter zone or segment 12. The distal port is normally an opening at the distal tip of the system so that the catheter device of the invention can be advanced over a guidewire that has been previously inserted and navigated through the vascular system of the subject to the vicinity of the area or segment of interest to be treated.

The catheter system itself, as seen in FIG. 1, is generally divided into six zones or longitudinal segments, the most proximal of which is the peripheral interface zone 22 which further contains intrusion sealing hub 24. The remaining zones are pictured in FIGS. 2–6 and represent multi-lumened segments of an elongated tubular catheter. The electrical port 26 connects to an insulated platinum wire 126 embedded within the substance of the polyethylene material (FIGS. 2–4) and used in association with an electrode described below. The remaining ports are extensions of four other lumens within the endothelial deployment device as will be discussed below. The catheter itself may preferably be constructed of quadraxially extruded polyethylene tube providing the desired number, size and configuration of internal lumens. Of course, it is contemplated that other materials and techniques of manufacture may more appropriately be employed if indicated.

Zones 14 and 18 consist of the proximal and distal balloons, respectively. The separation between the balloons defines the vascular span occluded when the balloons are inflated and includes the diffusion chamber. Inflation of these balloons is accomplished using a radiopaque contrast solution which is infused to the balloon 14 through the proximal balloon inflation lumen 130 and distal balloon zone 18 is inflated via the distal balloon inflation lumen 132. Radiopaque marker bands are used to define the center of each balloon as at 42 and 44. This aids in navigation of the catheter to precise placement in the vascular system. The balloons typically measure 6 mm in length and inflated balloons conform generally to an ellipsoid shape. The maximum diameter occurs at the center of the balloon which, when fully inflated, may measure approximately 2–5 mm. They are manufactured according to known technology from a relatively non-compliant polyethylene blended polymer, polyethylene terephthalate (PET), nylon, or other material in a well-known manner.

The elliptical design of the particular balloons used with the endothelial deployment device of the present invention affords minimal compression of the vascular surfaces upon inflation of the balloons while accomplishing physical interruption of blood flow between the balloons. Thus, it is not the purpose of the balloons in the present invention to compress stenoses as is generally the case with typical angioplasty devices, but merely to interrupt blood flow so that the desired drug/cell infusion operation can take place without exposure to flowing fluid. Manometers or other well-known pressure monitoring devices (not shown) are connected to monitor the balloon inflation pressure.

Segments or zones 12 and 14 are shown in greater detail in the enlarged fragmentary view of FIG. 2. Zone 12 typically measures approximately 840 mm in length and extends from the distal aspect of hub 24 to the origin of the proximal balloon zone 14. Approximately 25 mm of the distal end provides the input access for the vascular flow to bypass zones 14, 16 and 18. This portion of zone 12 contains a plurality of perfusion inflow ports which are directly connected to the guidewire/-perfusion lumen 134 (FIG. 3). One successful embodiment uses two series of six serially spaced perfusion inflow ports 40, one series of which is illustrated in FIG. 2. Typically, the perfusion inflow ports are approximately 0.5 mm in diameter and spaced about 4.0 mm apart.

The most distal zone of the device 20 in one embodiment extends 26 mm in length from the terminal portion of the distal balloon zone 18 to the distal tip marked by a radiopaque band 46 of the endothelial deployment device. The outer diameter of distal zone 20 tapers from approximately 1.5 mm at its origin to about 1.2 mm at the distal terminal end. The zone 20 is provided with a plurality of spirally arranged outflow perfusion ports 48 to return the bypassed fluid to the vascular passage of interest each measuring approximately 0.5 mm in diameter, it being further understood that the terminal end or distal end may also be open to reduce flow restriction and accommodate the guidewire. Each of the outflow ports 48 is connected directly to lumen 234 which is an extension of lumen 134 but of slightly different crossectional character and the outflow ports are separated from each other by approximately 4 mm. A radiopaque tip marker band 46 similar to those associated with the midpoints of the proximal and distal balloon zones 14 and 18 at 42 and 44 is provided.

It will readily be appreciated that blood flowing directly into lumen 134 in the distal portion of zone 12, then, bypasses 14, 16 and 18 and exits through the openings 48 and the tip in zone 20. In this manner, the blood flow entirely bypasses the segment of the vessel of interest separated and occluded by balloons 14 and 18, i.e., zone 16. Of course, should the catheter be used to address a vessel in which the flow is in the opposite direction, the bypass system will accommodate reverse flow.

An important aspect of the invention is the dispersion system associated with zone 16. Zone 16 includes the dispersion chamber by means of which the drug/cell infusion and implantation takes place in accordance with the invention. Zone 16 is typically approximately 22 mm in length but may vary according to clinical needs. The dispersion chamber is supplied via port 28 which continues through zone 12 in the form of lumen 128 (FIG. 3) and, in zone 16, the lumen at 228 (FIG. 5) takes the form of a kidney-shaped crossection having an outer arc consuming up to approximately 240° of the circumference of the catheter as shown at 228 in FIG. 5. The dispersion chamber of zone 16 is designed as a closed well system, isolated from the other distinct spaced parallel lumens within the catheter system. The dispersion system of lumen 228 is used to deploy the endothelial cell culture and growth activators and inhibitors as well as medicinal materials as desired. The dispersion chamber communicates with the isolated vascular segment between balloon zones 14 and 18 through a plurality of perforations 50 in the wall of the catheter defining the lumen 228 which typically are arranged in a rectangular pattern and measure approximately 250 microns (μm) in diameter and are spaced about 500 μm apart.

The exterior portion of the chamber is coated with a similarly perforated thin platinum foil member or platinum mesh screen 52 having perforations or openings 54 which are open to the exterior of the catheter. The platinum further serves as an electrode to produce an electric current or field using power originating from an external source connected to the input 26 and from there to the platinum foil or mesh via isolated conductor 126. The single platinum wire 126 typically measures approximately 100 μm in diameter and is preferably isolated by being embedded in the substance of the polyethylene or other catheter construction material and thereby also being electrically insulated from the other structures in the endothelial deployment device.

Materials to be deployed from the dispersion chamber are infused through the drug/cell infusion port 28, conducted through the several connected continuing lumen shapes as at 128 to the dispersion chamber lumen 228 in zone 16 where they are distributed via the openings 50 and 54 to the vascular site of interest. The electrical field or current may be advantageously used in the deployment of the biologically active materials, specifically, the vascular endothelial cells, or in the delivery of specific biologic/pharmacologic agents.

The distal aspect of the dispersion chamber segment or zone 16 contains a one-way pressure relief valve 56 (FIG. 4) which is approximately 400 μm in diameter and which remains closed unless relative pressure within the occluded vascular segment exceeds a predetermined maximum, typically 100 mm Hg. The valve, of course, prevents vascular damage due to inadvertent overpressurization of the vessel of interest during infusion into segment 16.

The typical overall length of the endothelial device of the invention is approximately 1,115 mm and may be delivered over a guidewire into a blood vessel of interest using any one of several guiding catheter devices. The marker bands, of course, are used in conjunction with fluoroscopic observation to permit accurate vascular navigation of the distal tip of the device as well as the centers of the proximal and distal balloons for more precise positioning in the vascular system of the location of the segment to be treated.

Figure 7:
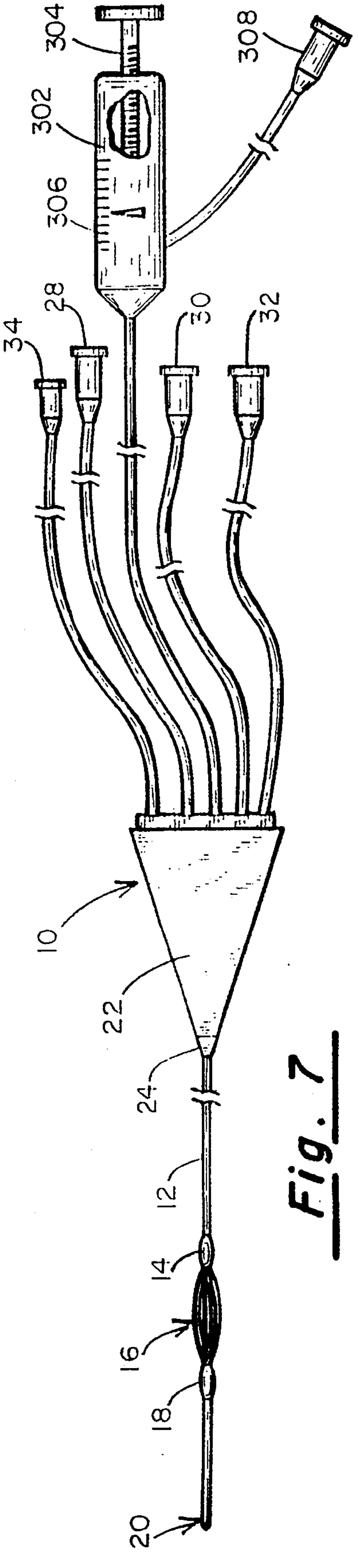
FIG. 7 is an overall schematic view of an alternate embodiment of the endothelial deployment catheter device of the invention broken away where inordinate lengths are involved and cut away to show details.

FIGS. 7–10 depict an alternative embodiment of the active biological material deployment device of the invention. In this regard, FIG. 7 depicts an overall schematic representation of a device substantially similar in character to that of FIG. 1 save the provision of an array of flexible conductors 300 associated with the zone 16 which may replace the platinum foil member or platinum mesh screen and a corresponding proximally connecting operative handle means generally at 302 including an axially displaceable element or system 304 which may include a control wire or other member (not shown) operably connected with the collective array of wires 300 with actuator calibrated at 306. An electrical connector to provide electrical energy to the array 300 is shown at 308. The actuator 304 may be a lockable plunger knob having a gauged stem and capable of being locked at any desired position or other similar means, for example, a threaded member which may be rotated to produce the desired calibrated longitudinal displacement to the element 304.

The wire elements of the bundle or array of wire elements are normally arranged symmetrically about the axis of the dispersion zone 16. While any desired number can be employed, one embodiment uses six such elements. Also, the electrical energy supplied is normally direct current; however, it is contemplated that the system could be adapted to use alternating current by one skilled in the art.

Figure 9:
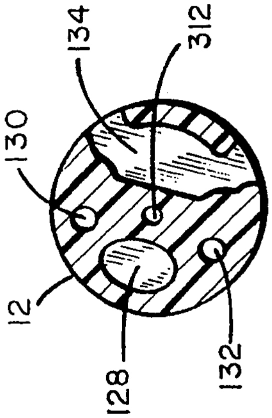
FIG. 9 is an enlarged sectional view taken along 9—9 of FIG. 8.

The element 304 is, in turn, connected via an operating element 305 to a proximal element retainer and connector means 310 in the lumen through which the individual conductor elements 300 of the array are also collectively channeled (FIGS. 8 and 10) via internal lumen 312 (FIG. 9). The calibrated actuator 306 is operable to apply bidirectional axial force to the array of conductor elements 300 in a manner which, in one embodiment, causes the elements to fan out or retract collectively in accordance with the axial displacement of the actuator 306. A distal retainer means 314 is also provided to which the distal ends of the conductor elements are also fixed. Electrical connection to the array of conductors 300 may be via member or connector 308 or other means connecting to the conductors at the proximal ends thereof either individually or collectively. In this manner, as illustrated in FIGS. 8 and 10, the plurality of conductors of the array 300 do not have a fixed linear distance between 310 and 314 such that the axial displacement of the proximal ends relative to the distal retainer 314 produces an outward radial flexure or relatively uniform radial expansion of the array of conductors 300 as the member 306 is displaced inward and, correspondingly, produces a straightening of the conductors as the member 306 is displaced outward.

Figure 8:
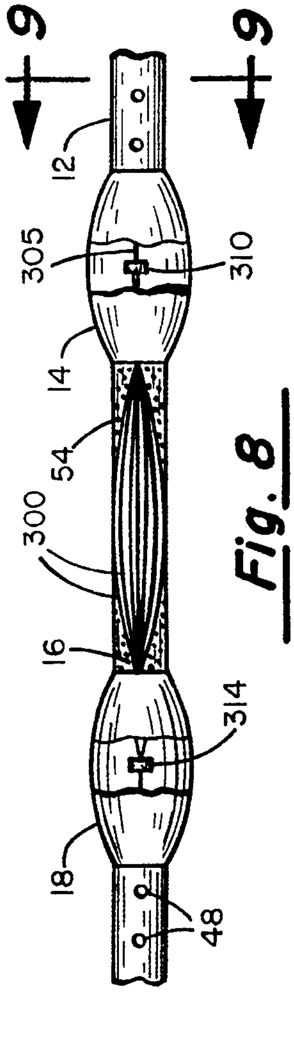
FIG. 8 is an enlarged fragmentary side view of the central zones of the catheter portion of the device of the embodiment of FIG. 7.
Figure 10:
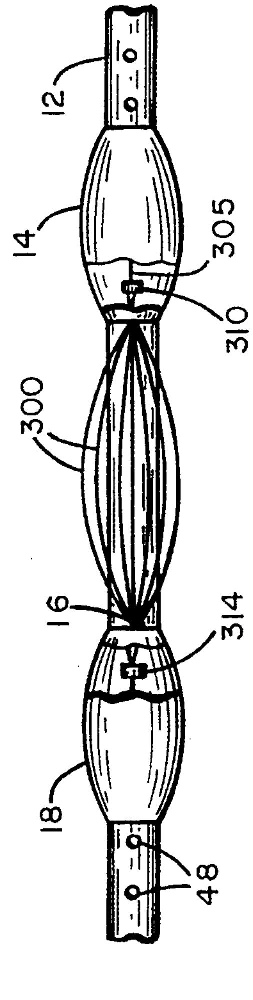
FIG. 10 is a view similar to FIG. 8 with the conductor array radially deployed.

The fragmentary FIGS. 8 and 10 depict deployment zone 16 flanked by proximal and distal balloons 14 and 18, respectively. FIG. 8 depicts the uninflated, undeployed state utilized for vascular navigation and FIG. 10 illustrates the inflated, deployed position for implantation of a biologically active species. The array of conductors 300 may subtend any desired angle about the periphery of the zone 16 and typically subtend an angle equal to or greater than that subtended by the dispersion openings 54 in the dispersion zone 16 (FIG. 4). The controlled expansion and contraction of the radially deployable array of conductors 300 allows for the uniform and proximate application of the desired electrical field to be controlled at the site of implantation of the biologically active species, which may be endothelial cells.

This embodiment allows a substantially greater amount of control over the placement and uniformity of the electric fields and so may, in fact, reduce the time required for successful implantation and thereby reduce the time required for the procedure to be completed. It should further be understood, however, that whereas uniformity is generally desired, asymmetry may also be introduced into the character of radial expansion of the conductor elements, as by using varying lengths, if desired. While there is no limitation on the particular number of radially deployable conductors, embodiments using six conductors have been successfully built.

The procedure for operation of the system of the invention begins with inserting the catheter preloaded with the guidewire through a guide catheter into the arterial system of the subject, typically through the femoral artery. A guidewire is advanced through the vascular system via the guide catheter until the guidewire tip reaches a point at or just beyond the vascular segment of interest. This is typically beyond the location of a stenosis or lesion which has just been subjected to a balloon angioplasty or atherectomy procedure. At this point, a portion of the guidewire, of course, still extends through the guide catheter to a point outside the body. The endothelial deployment device of the invention can then be advanced over the wire so that the wire is passed through the hollow lumen beginning at the distal end and through the lumen sequence 234, 134 and protruding out of guidewire port 34 or other proximal guidewire port opening.

The multi-lumenal catheter system of the endothelial deployment device of the invention is then advanced over the wire through the vascular system to the site of the vascular segment of interest. In accordance with the invention, the radiopaque markers 42 and 44 can be used to properly align the balloons 14 and 18 flanking the vascular segment of interest. Once the system is in place, the balloons 14 and 18 can be inflated by introducing fluid into the proximal and distal balloon ports which are connected to a fluid source in a well-known manner.

Once the balloons are properly inflated, a bypass blood flow is established. The guidewire is withdrawn to allow maximum flow through the perfusion ports, the blood flow in the vascular segment between the proximal and distal balloons of the endothelial deployment device having been physically interrupted so that the walls of the vascular segment to be treated are temporarily removed from the path of flowing fluid. The establishment of this relatively quiescent condition is a prerequisite to endothelial cell implantation and adequate delivery of other biologic/pharmacologic agents.

The perforated platinum foil electrode or the array of radially dispersed flexible conductors disposed between the dispersion chamber and the segment of vessel of interest can now be energized in any desired manner. For example, the wire 126 may be used to deliver current in a constant or pulsed fashion which may be triggered by the patient's own ECG complex via an electrical stimulator. Duration of the current may be adjusted such that a pulse of current is initiated on a peak of the patient's R- wave and terminated prior to the vulnerable period of repolarization (e.g., the ascending slope of the T wave). This is done in conjunction or just following deployment of biologically active materials introduced via port 28 and lumens 128 and 228 and ultimately through the openings 50 and 54 in the dispersion chamber segment 16 and platinum foil. In accordance with a main application of the invention, the biologically active materials typically contain an endothelial cell culture together with other materials to promote and establish attachment and growth.

Inasmuch as cultured endothelial cells may preferably migrate toward a variably charged electrode, by variably charging the platinum foil, the vascular segment of interest may have a slight charge. It is, of course, understood that an exterior electrical common exists in order to complete such an electrical circuit. This may aid in the delivery of endothelial cells or other biologic/pharmacologic agents to the wall of the vascular segment of interest. Replication of the electrical charge together with the maintenance of the occluded or flow-free state of the vascular segment may promote the tendency of the endothelial cells to adhere to the surface of the interior of the vessel of interest. In this manner, the endothelial cells may be able to attach and resume normal biological activity such that they will not be dislodged and swept away by normal blood flow. At this point, the guidewire is again advanced beyond the vascular space of interest and the proximal, distal balloons deflated and the deployment device removed by reversing the insertion steps.

By using the device of the invention, the endothelial cells or other biologically active material can be readily dispersed to the vascular segment of interest, in vivo, using the flow bypass system. Cell adherence may be sped up by applying the electric charge during the deployment step. Subsequent normal growth should reestablish normal vascular endothelium and prevent or retard restenosis in the vascular segment involved.

This invention has been described in this application in considerable detail in order to comply with the Patent Statutes and to provide those skilled in the art with the information needed to apply the novel principles and to construct and use such specialized components as are required. However, it is to be further understood that the invention can be carried out by specifically different equipment and devices and that various modifications can be accomplished without departing from the scope of the invention itself.

We claim:

1. A method of providing iontophoretic transport to deliver selected biologically and/or pharmacologically active material to a selected vascular segment of a patient of interest to restore vascular endothelium vitality in such specific segments of blood vessels comprising the steps of:

(a) determining a selected vascular segment of a patient of interest to be treated;

(b) introducing a vascular catheter device into the vascular system of the patient of interest;

(c) navigating said vascular catheter device to said selected vascular segment, said catheter device having spaced lumen-inflatable balloon elements expansible against vessel walls to occlude blood flow therebetween, lumen supplied delivery chamber having openings for delivering biologically and/or pharmacologically active species to the vascular segment between the balloon elements, externally connected lumen means for inflating said balloon elements and supplying said delivery chamber, expandable electrical charge carrying means on said catheter for providing and delivering an electrical field in the vicinity of and during the deployment of the biologically active species, means connected to said electric charge carrying means for expanding the expandable electrical charge carrying means and blood flow bypass means in said vascular catheter establishing an alternate path for flow about the occluded vascular segment;

(d) expanding said balloon elements to occlude flow in the selected vascular segment and establishing bypass flow;

(e) expanding the expandable electrical means as desired;

(f) providing an amount of selected biologically and/or pharmacologically active material to said lumen supplied delivery chamber;

(g) dispersing the biologically and/or pharmacologically active species while using the expanded electrical charge carrying means to deliver a charge to produce an electrical field to a desired area of occluded vascular segment;

(h) maintaining said flow occlusion for a predetermined time necessary for the biologically and/or pharmacologically active species to be sufficiently assimilated to be unaffected by resumed normal vascular flow; and (i) deflating the balloons and retracting the expandable electrical means restoring normal vascular flow and removing the catheter device.

2. The method of claim 1 wherein the biologically active species includes endothelial cells and further comprising the step of modulating the electrical field during the dispersion step.

3. The method of claim 2 wherein said charge is delivered in a time-variable manner.

4. The method of claim 3 wherein said charge is delivered in a mode selected from the group consisting of pulsed or constant.

5. The method of claim 4 wherein the charge applied is selected from the group consisting of negative or positive charge.

6. The method of claim 1 wherein the charge applied is selected from the group consisting of negative or positive charge.

7. The method of claim 1 further comprising the step of adjusting the amount of expansion of the expandable electrical means as required.

8. A system for the deployment of biologically/pharmacologically active material in vascular wall tissue of a selected vascular segment, comprising an elongated multi-lumen catheter system further comprising:

(a) a pair of spaced, fluid-inflatable balloon elements attached to said multi-lumen catheter and inflatable by means of connected lumens therein, said pair of spaced inflatable balloon elements occluding normal vascular blood flow in said selected vascular segment when expanded against adjacent vascular walls;

(b) an externally accessed deployment region in said catheter between said inflatable balloon elements further comprising:

(1) deployment chamber having a plurality of openings therein for delivering biological and/or pharmacologically active materials to the vascular wall; and (2) radially expandable electrical charge delivery means for applying a controlled electric field in the vicinity of deployment of the biologically and/or pharmacologically active materials;

(c) flow by-pass means in said multi-lumen catheter for providing a path for allowing vascular flow to by-pass said selected vascular segment when normal flow is occluded;

(d) a plurality of lumen means in said multi-lumen catheter for supplying balloon inflation fluid to said balloon elements and said biologically and/or pharmacologically active materials to said deployment chamber;

(e) charge delivery deployment control means for controlling the radial expansion of said radially expandable electrical charge delivery means; and (f) means for supplying electrical energy to said radially expandable electrical charge delivery means.

9. The system of claim 8 wherein said radially expandable electrical charge delivery means further comprises a plurality of radially spaced, external flexible conductors extending along the deployment region and further comprising means for radially constraining said conductors in relation to said catheter distal and proximal the deployment region so that they assume an arcuate posture when expanded.

10. The system of claim 9 wherein said plurality of radially spaced conductors form a substantially symmetrical bundle.

11. The system of claim 10 wherein said charge delivery deployment control means further comprises means for fixing radial expansion at any desired position.

12. The system of claim 10 wherein the number of radially spaced conductors is six.

13. The system of claim 9 wherein:

(a) said plurality of lumen means comprises an infusion lumen, said deployment chamber being part of said infusion lumen and subtending a major arc of vascular circumference;

(b) said plurality of openings in said deployment region comprises a pattern of perforations disposed in said deployment chamber; and (c) wherein said radially expandable charge delivery means further subtends an arc of vascular circumference equal to or greater than that of said deployment chamber.

14. The system of claim 9 wherein:

(a) said means for radially constraining said conductors comprises retention means including proximal and distal retention means for radially constricting expansion of said conductors at points flanking said deployment region; and (c) wherein said conductors comprise an array of wire elements fixed to said proximal and distal retention means such that the relative linear displacement of the proximal and distal wire retention means produces arcuate radial expansion or retraction of the conductor elements.

15. The system of claim 14 wherein said charge delivery deployment control means further comprises an externally operable control element having connected calibrated means for relatively axially displacing the proximal and distal retention means relative to each other thereby enabling precisely controlled outward flexure or straightening of said array of wire elements.

16. The system of claim 15 wherein said means for applying electrical energy to said electrical charge delivery means further comprises control means capable of time-variable modulation including optionally pulsing of the applied electrical field.

17. The system of claim 15 wherein said means for applying electrical energy to said electrical charge delivery means further comprises control means capable of time-variable modulation including optionally pulsing of the applied electrical field.

18. The system of claim 17 wherein said charge delivery deployment control means comprises an axially displaceable wire and calibrated actuating handle means.

19. The system of claim 15 wherein the externally operable deployment element comprises an axially displaceable wire and calibrated actuating handle means.

20. The system of claim 8 wherein said charge delivery deployment control means further comprises control element means connected to said radially expandable charge delivery means and operable from outside said catheter for radially expanding and retracting said charge delivery means.

21. The system of claim 20 wherein said charge delivery control means further comprises means for fixing radial expansion at any desired position.

22. The system of claim 8 wherein said means for supplying electrical energy to said electrical charge delivery means further comprises control means capable of time-variable modulation including optionally pulsing of the applied electrical field.

23. A multi-lumen catheter system for the deployment of biologically and/or pharmacologically active material in vascular wall tissue of a selected vascular segment comprising:

(a) an elongated multi-lumen catheter including a plurality of externally accessible lumens;

(b) an externally accessed deployment region in said catheter adapted to address a selected vascular segment and having a dispersion lumen chamber subtending a predetermined arc of the vascular circumference provided with a pattern of openings for deploying biologically and/or pharmacologically active materials in a selected vascular segment supplied through a connected one of said externally accessible lumens;

(c) radially expandable charge delivery means for applying a controlled electrical field at the point of deployment of the biologically active material further comprising:

(1) an array of radially spaced, external flexible wire conductor elements extending along the deployment region;

(2) constraining means for radially constricting said conductors comprising common proximal and distal end constraining means flanking said deployment region;

(3) wherein said conductor elements are fixed to said constraining means; and (4) an externally operable calibrated deployment element connected to the proximal retention means for axially displacing the proximal retention means relative to the distal retention means in a controlled manner thereby causing outward arcuate flexure or straightening of the array of wire elements;

(d) a pair of spaced, fluid-inflatable balloons fixed to said catheter and flanking said deployment region for temporarily occluding normal vascular blood flow in the selected vascular segment during deployment of the biologically and/or pharmacologically active materials;

(e) flow by-pass means in said multi-lumen catheter comprising a lumen connecting proximal and distal infusion port zones for maintaining at least a minimum blood flow about and beyond said selected vascular segment during the occlusion thereof;

(f) lumen means in said multi-lumen catheter for supplying said biologically and/or pharmacologically active materials to said deployment chamber;

(g) means for supplying electrical energy to said radially expandable electrical charge delivery means; and (h) control interface means for controlling operation of the system including externally operated means capable of modulating the charge applied by the charge delivery means.

24. The system of claim 23 wherein said means for controlling the radial expansion of said charge delivery means further comprises means for fixing the radial expansion at any desired position.

* * * * *

UNITED STATES PATENT AND TRADEMARK OFFICE

CERTIFICATE OF CORRECTION

PATENT NO. : 5,423,744

DATED : June 13, 1995

INVENTOR(S) : Nelson Gencheff et al

It is certified that error appears in the above-indentified patent and that said Letters Patent is hereby corrected as shown below:

In column 14, line 27, delete "(c)", and insert -- (b) -- .

In column 14, line 63, after "delivery", insert -- deployment -- .

Signed and Sealed this

Twenty-ninth Day of August, 1995

Attest:

BRUCE LEHMAN

Attesting Officer

*Commissioner of Patents and Trademarks*